(12) United States Patent
Maeda

(10) Patent No.: US 7,149,571 B2
(45) Date of Patent: Dec. 12, 2006

(54) PORTABLE BIOLOGICAL DATA MEASURING APPARATUS

(75) Inventor: Tatsuo Maeda, Fukuoka (JP)

(73) Assignee: Parama Tech Co., Ltd., Fukuoka (JP)

(*) Notice: Subject to any disclaimer, the term of this patent is extended or adjusted under 35 U.S.C. 154(b) by 472 days.

(21) Appl. No.: 10/294,550

(22) Filed: Nov. 15, 2002

(65) Prior Publication Data

US 2003/0097078 A1    May 22, 2003

(30) Foreign Application Priority Data

Nov. 16, 2001    (JP)    ............... 2001-351314

(51) Int. Cl.
*A61B 5/04*    (2006.01)

(52) U.S. Cl. ..................... 600/523; 600/509

(58) Field of Classification Search ................ 600/509, 600/522, 523
See application file for complete search history.

(56) References Cited

U.S. PATENT DOCUMENTS

| | | |
|---|---|---|
| 4,550,735 A | 11/1985 | Akamatsu et al. |
| 5,226,425 A | 7/1993 | Righter |
| 5,746,207 A * | 5/1998 | McLaughlin et al. ........ 600/372 |
| 6,149,602 A | 11/2000 | Arcelus |
| 6,370,423 B1 * | 4/2002 | Guerrero et al. ............ 600/513 |

FOREIGN PATENT DOCUMENTS

| | | |
|---|---|---|
| CN | 1289240 A | 3/2001 |
| JP | 60-99234 A | 6/1985 |
| JP | 02-206431 A | 8/1990 |
| JP | 03-091305 U | 9/1991 |
| JP | 04-025701 U | 2/1992 |
| JP | 05-154117 A | 6/1993 |
| JP | 09-056686 A | 3/1997 |
| JP | 10-314134 A | 12/1998 |

* cited by examiner

*Primary Examiner*—Scott M. Getzow
(74) *Attorney, Agent, or Firm*—Sughrue Mion, PLLC

(57) ABSTRACT

To provide a portable biological data measuring apparatus capable of measuring, storing and displaying biological data of a human being, in particular. The apparatus includes a GND electrode (12B) and a minus electrode (12C) which are provided on the opposite side faces of a roughly rectangular parallelopiped-shaped chassis (11), and a plus electrode (12A) provided on the face curved into an elliptical arc shape in cross section and adjacent to the opposite faces on which the GND electrode (12B) and the minus electrode (12C) are provided, in which biological data is measured using the plus electrode (12A), the GND electrode (12B) and the minus electrode (12C).

4 Claims, 6 Drawing Sheets

FIG. 3
(a)
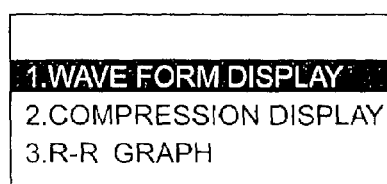
DECISION
CANCELLATION
(b) CANCELLATION
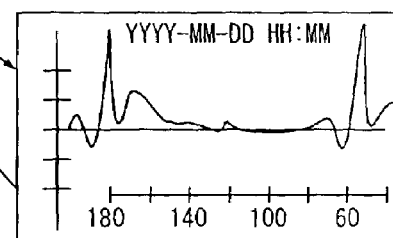
[◁ ▷]
DECISION
(c) CANCELLATION
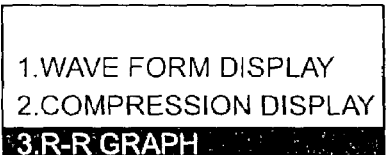
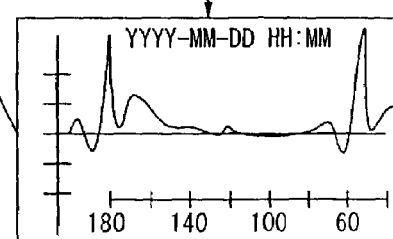
CANCELLATION
DECISION
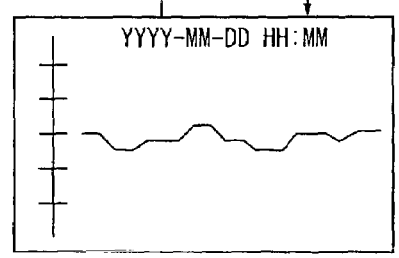
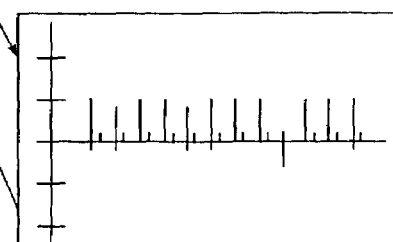

PORTABLE BIOLOGICAL DATA MEASURING APPARATUS

BACKGROUND OF THE INVENTION

1. Field of the Invention

The present invention generally relates to a portable biological data measuring apparatus. In particular, the invention relates to a novel improvement for enabling biological data to be processed and displayed on the side of a portable apparatus.

2. Description of the Related Art

As for the structure of an apparatus of this sort which has been conventionally used, there can be given as an example the structure of an adapter for controlling biological risk, as shown in FIG. 6, described in JP 9-173304 A for example. That is to say, referring to FIG. 6, an A-type adapter for controlling an organism designated by reference character 1A includes a sensor unit 5 and a modem 3, and is adapted to measure biological data such as a body temperature, electrocardiograph and an heartbeat. A flexible rod 4 has the sensor unit 5 including an electrode 5a and a thermistor 5e at the tip portion thereof, and is stretchably accommodated in a housing of the modem 2. In the figure, reference numeral 3 designates a power source switch, and reference numeral 6 designates a clock setting button. The measurement of the electrocardiographic data is carried out with the electrodes 5a to 5c. Reference numeral 7 designates a measurement button, reference numeral 8 designates a transmission button, reference numeral 9 designates a display unit, and reference numeral 10 designates a plug for connection to a mobile phone. With use of the measurement units and the transmission units, it is therefore possible to readily undergo the biological risk control with the mobile phone as a medium.

Since the conventional apparatus is constructed as described above, it has the following problem. That is to say, even if the biological data can be measured, it is impossible to process or display the data on the apparatus side.

SUMMARY OF THE INVENTION

In the light of the foregoing, the present invention has been made in order to solve the above-mentioned problem associated with the prior art, and it is, therefore, an object of the present invention to provide a portable biological data measuring apparatus capable of particularly, measuring, storing, and displaying biological data of a human being.

According to the present invention, a portable biological data measuring apparatus includes a GND electrode and a minus electrode which are provided on the opposite side faces of a roughly rectangular parallelopiped-shaped chassis, and a plus electrode provided on the face curved to have a semi-ellipse shape and adjacent to the opposite faces on which the GND electrode and the minus electrode are provided, in which biological data is measured using the plus electrode, the GND electrode and the minus electrode. In addition, the portable biological data measuring apparatus further includes display means for displaying thereon the biological data, in which a first R wave and a second R wave contained in an electrocardiographic waveform are displayed on the display means, and in which an axis for reading-out of the number of heartbeats on which data representing the number of heartbeats is plotted is displayed on the axis of abscissa indicating a time base with the peak portion of the first R wave being set as a reference point. In addition, the portable biological data measuring apparatus further includes display means for displaying thereon the biological data, in which an electrocardiographic waveform is displayed on the display means with the waveform being compressed in the direction of a time base. Moreover, the portable biological data measuring apparatus further includes display means for displaying thereon the biological data, in which the data representing the time transition of the number of heartbeats between the adjacent R waves is displayed on the display means.

BRIEF DESCRIPTION OF THE DRAWINGS

The foregoing and other objects are effected by the invention as will be apparent from the following description and claims taken in connection with the accompanying drawings, forming a part of this application, in which:

FIG. 3 is a diagram showing conceptually the flow of a data processing in the portable biological data measuring apparatus according to the present invention;

DETAILED DESCRIPTION OF THE PREFERRED EMBODIMENT

The preferred embodiment of a portable biological data measuring apparatus according to the present invention will hereinafter be described in detail with reference to the accompanying drawings.

Figure 1:
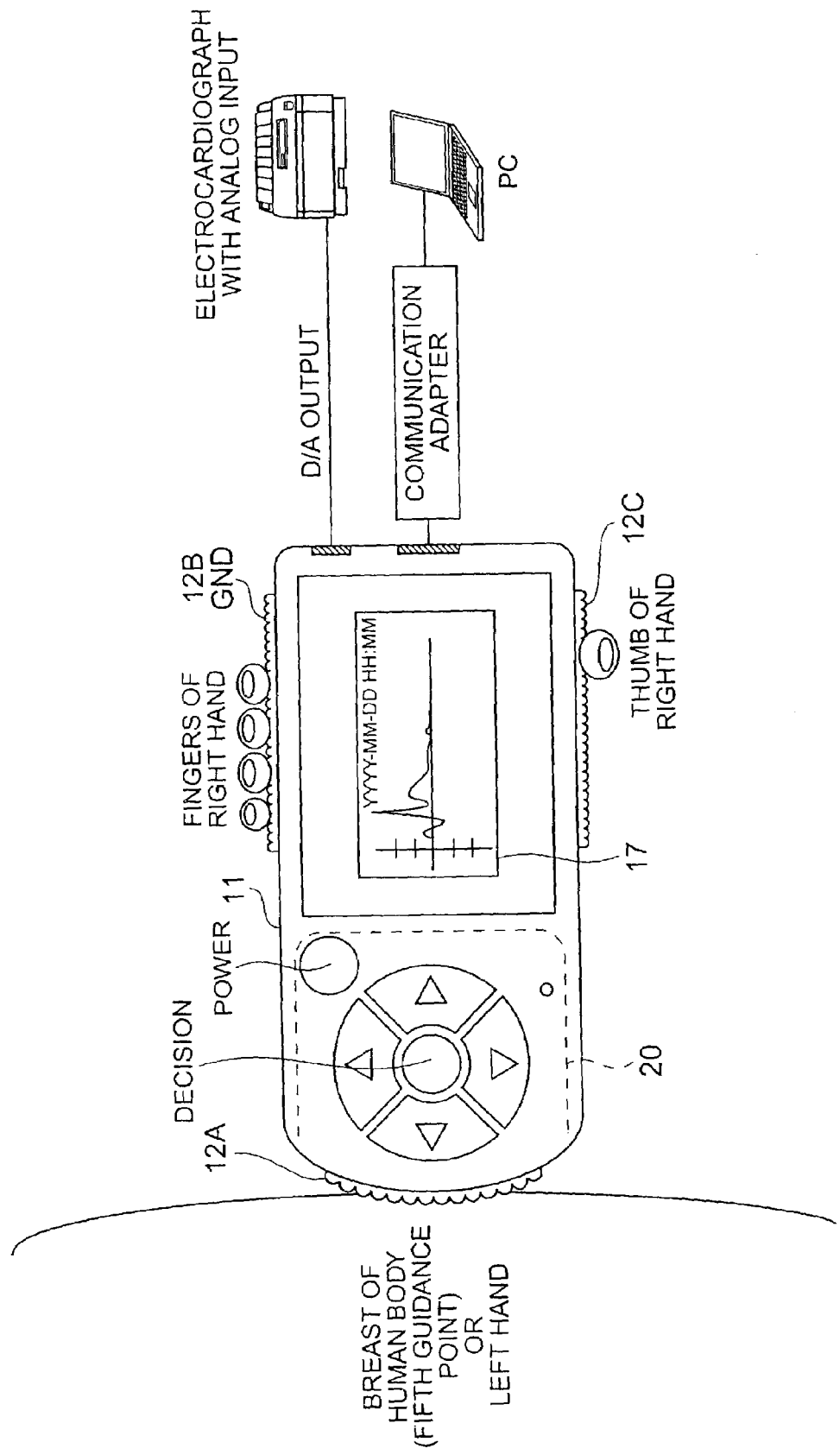
FIG. 1 is a diagram schematically showing a structure of a portable biological data measuring apparatus according to the present invention.

Referring now to FIG. 1, a portable biological data measuring apparatus according to the present invention includes a plus electrode 12A, a GND electrode 12B and a minus electrode 12C on the side faces of a rectangular parallelopiped-shaped chassis 11. The GND electrode 12B and the minus electrode 12C are respectively provided on the opposite side faces of the chassis 11, and the plus electrode 12A is provided on the face which defines one longitudinal end of the chassis 11 and is located between the GND electrode 12B and the minus electrode 12C.

That is to say, the apparatus is configured in such a way as to be able to measure the value of the voltage developed across the plus electrode 12A and the GND electrode 12B, and the value of the voltage developed across the GND electrode 12B and the minus electrode 12C using these electrodes 12A to 12C.

In such a portable biological data measuring apparatus, as shown in FIG. 1, if the plus electrode 12A is touched on a predetermined position of the breast of the human body or a left hand while respectively holding the GND electrode 12B and the minus electrode 12C with the four fingers (from the index finger to the little finger) other than the thumb of a right hand, and the thumb of the right hand, then it is possible to measure the value of the voltage developed across the plus electrode 12A and the GND electrode 12B, and the value of the voltage developed across the GND electrode 12B and the minus electrode 12C. Thus, the voltage value of an R wave is measured by utilizing the well known method, thereby making it possible to measure the electrocardiographic waveform and the number of heartbeats, of a human being, as the biological data.

It is preferable that the irregularity is formed in the surfaces of the electrodes 12A to 12C and also the plus electrode 12A is curved. By adopting such a structure, it is possible to stably measure an electrocardiographic waveform.

The curved shape is preferably a circumferential shape of a semi-ellipse which is 22 mm in long radius and is 11 mm in short radius. By adopting such a shape, the plus electrode 12A can be constructed into a shape which is easy to be fitted to the breast or a palm of a left hand of the human body.

In addition, the formation of the fine irregularity on the surfaces of the electrodes 12A to 12C makes possible the stable touch to the human body and also makes it possible to reduce the touch area to thereby enhance the noise resistance.

Figure 2:
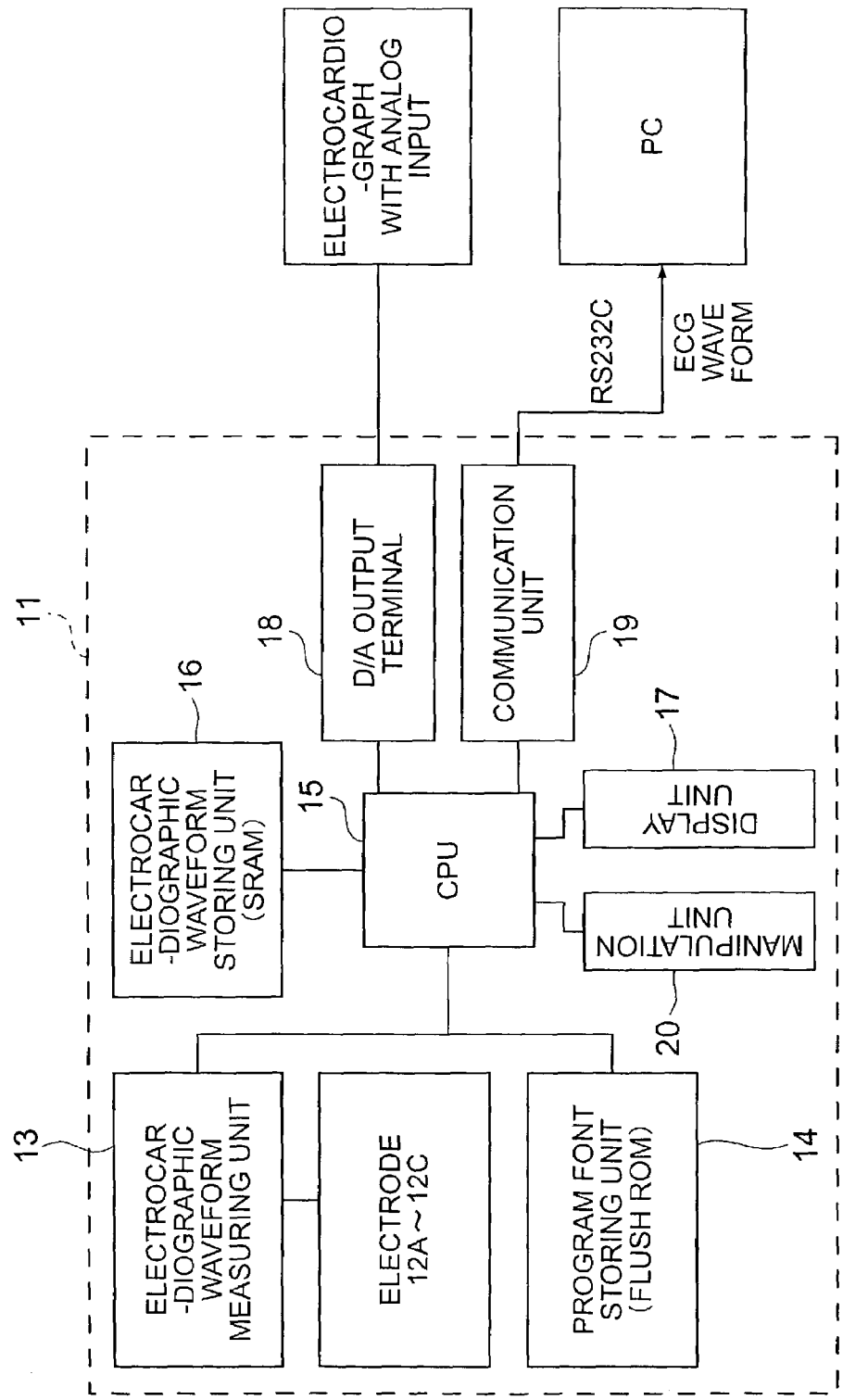
FIG. 2 is a block diagram schematically showing a system configuration of a portable biological data measuring apparatus according to the present invention.

FIG. 2 is a block diagram schematically showing a system configuration of the portable biological data measuring apparatus of the present invention.

As shown in FIG. 2, the portable biological data measuring apparatus of the present invention includes: an electrocardiographic waveform measuring unit 13 for measuring an electrocardiographic waveform from a voltage signal obtained with the electrodes 12A to 12C; a program font storing unit 14 including, for example, a flush ROM and the like and serving to store and hold a program font; a CPU 15; an electrocardiographic waveform storing unit 16 including, for example, an SRAM and serving to store and hold data of an electrocardiographic waveform; a display unit 17 including, for example, a graphic LCD and the like and serving to display thereon an electrocardiographic waveform; D/A output terminal 18 for outputting therethrough data of an electrocardiographic waveform to an electrocardiograph with an analog input in the outside; a communication unit 19 including a serial I/O unit and the like for transmitting data of an electrocardiographic waveform to an PC in the outside; and a manipulation unit 20 for receiving as its input various manipulation commands.

Note that the communication unit 19 does not need to be necessarily provided.

FIG. 3 is a diagram showing conceptually the flow of a data processing in the portable biological data measuring apparatus of the present invention.

As shown in FIG. 3, with the portable biological data measuring apparatus of the present invention, it is possible to select among three modes: (a) a waveform display mode for display of an electrocardiographic waveform; (b) a compression display mode for confirmation of the situation of change in electrocardiographic waveform over a long period of time; and (c) an R—R graph display mode for display of the transition of the heartbeat between an R wave and an R wave (hereinafter, referred to as "between R—R" for short, when applicable).

First of all, the waveform display mode will hereinbelow be described.

Figure 4:
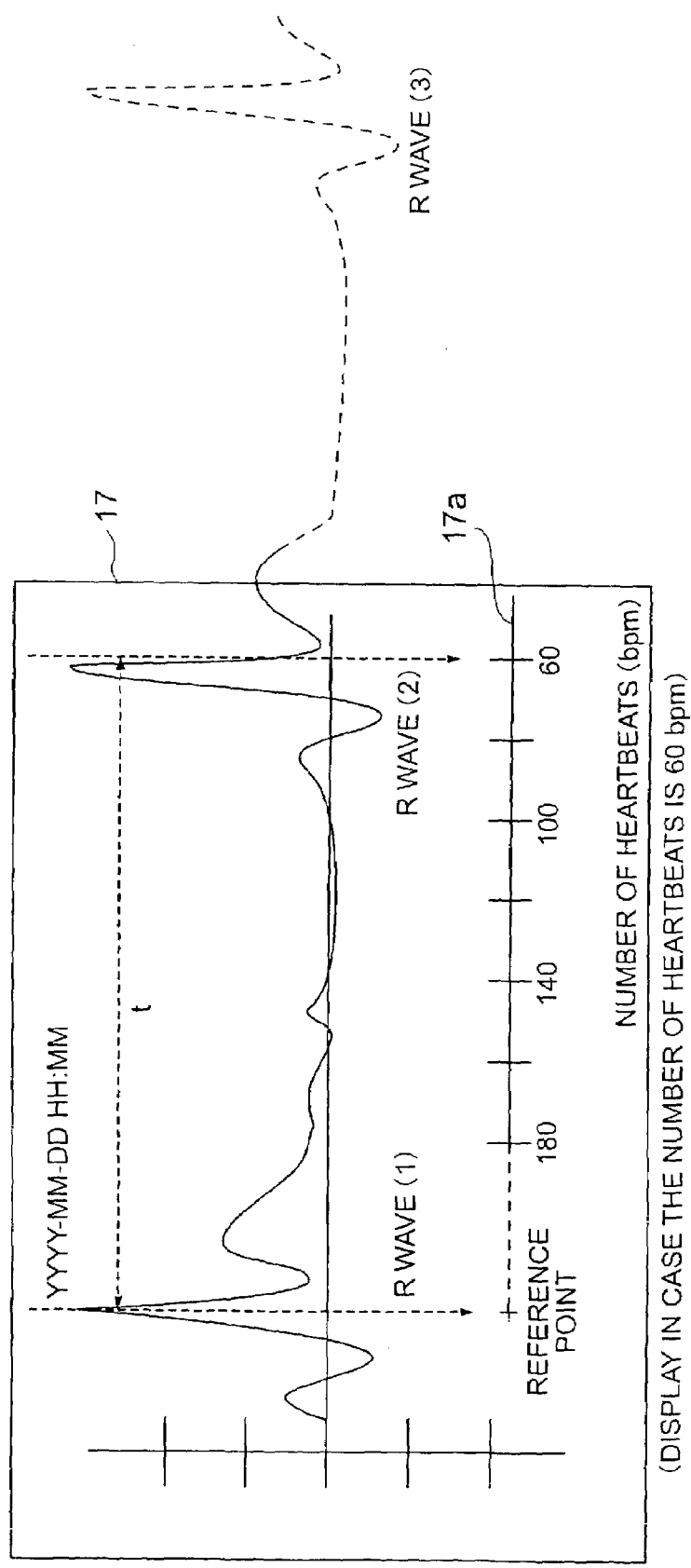
FIG. 4 is a diagram schematically showing the displayed contents of a display unit in a waveform display mode.

FIG. 4 is a diagram schematically showing the display contents of the display unit 17 in the waveform display mode.

In this case, the R waves of the electrocardiographic waveform which are measured in sequential timing will hereinbelow be referred to as a first R wave, a second R wave and a third R wave for the convenience of explanation. Thus, the first to third R waves do not point to a specific R wave contained in the electrocardiographic waveform, and such R waves are referred to as a first R wave, a second R wave, a third R wave, . . . , an n-th R wave in this order from the R wave which is firstly measured after start of the measurement.

As shown in FIG. 4, the peak of the first R wave (1) is adjusted to the reference point with an arrow button of the manipulation unit 20 to obtain time t ranging from the first R wave (1) to the second R wave (2) (hereinafter, referred to as "an R—R interval(s)" for short, when applicable). The number of heartbeats in calculation is calculated from the following Expression 1 using the R—R interval t. Note that the R—R interval t will be described later.

In addition, in the waveform display mode, an axis 17a for reading-out of the number of heartbeats as the axis of abscissa for reading-out of the number of heartbeats can be displayed on the display unit 17.

In general, the number of heartbeats can be obtained on the basis of the following Expression 1.

$$\text{The number of heartbeats } (bpm) = 1 \text{ minute } (60{,}000 \text{ ms})/\text{R—R interval } (t\text{ms}) \quad (1)$$

When the number of heartbeats is obtained as 180 bpm from Expression 1, after a lapse of 333.333 . . . (ms) from the reference point, the next R wave (2) is displayed.

Thus, in the case where for example, the displayable dots of the LCD of the display unit is W128 (width)×H64 (length), if a period of time which one dot occupies in the direction of the axis of abscissa is previously set, since the number of dots from the fixed reference point is in proportion to the elapsed time, it is possible to display the axis 17a for reading-out of the number of heartbeats.

Note that the above-mentioned R—R interval t (ms) can also be obtained by counting the number of dots between R—R.

That is to say, in the case where the numbers of heartbeats are 180 bpm, 120 bpm and 60 bpm, respectively, since the second R wave (2) is displayed after lapse of 333.333 . . . (ms), 66.666 . . . (ms) and 1,000 (ms) from the reference point, if the axis 17a for reading-out of the number of heartbeats on which the numeric values of 180 (bpm), 120 (bpm) and 60 (bpm) are plotted on these positions is displayed, it is possible to provide a portable biological data measuring apparatus which is capable of reading out instantaneously and readily the number of heartbeats on the display unit 17.

By carrying out the manipulation with the manipulation unit 20, if the next R wave, i.e., the second R wave (2) is selected as the reference point, then the R wave (2) will be displayed as the reference point on the display unit 17 and then the subsequent third R wave (3) will be displayed on the position corresponding to the number of heartbeats. Note that, while in FIG. 4, the third R wave (3) drops out to the right-hand side of the display unit 17 for the convenience of explanation, when the second R wave (2) is selected as the reference point on the display unit 17 by manipulating the manipulation unit 20, the waveform is moved to the left-hand side on the display unit 17, and thus the display can be carried out in such a way that the selected R wave is always located on the left-hand side on the screen. In such a manner, up to the n-th R wave can be selectively displayed on the display unit 17.

Next, the compression display mode will hereinbelow be described.

Figure 5:
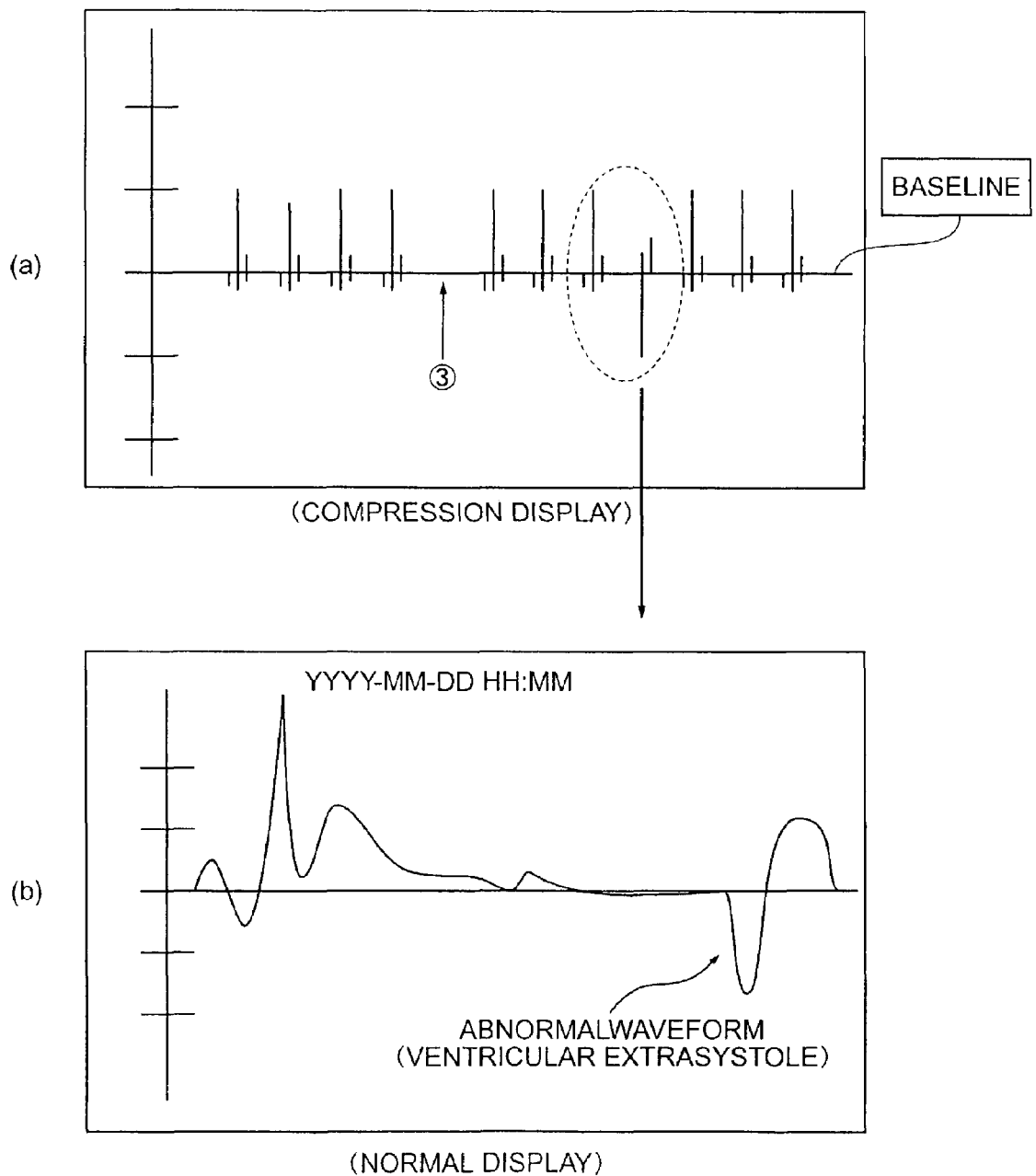
FIGS. 5A and 5B are respectively diagrams schematically showing the displayed contents of a display unit in a compression display mode.
Figure 6:
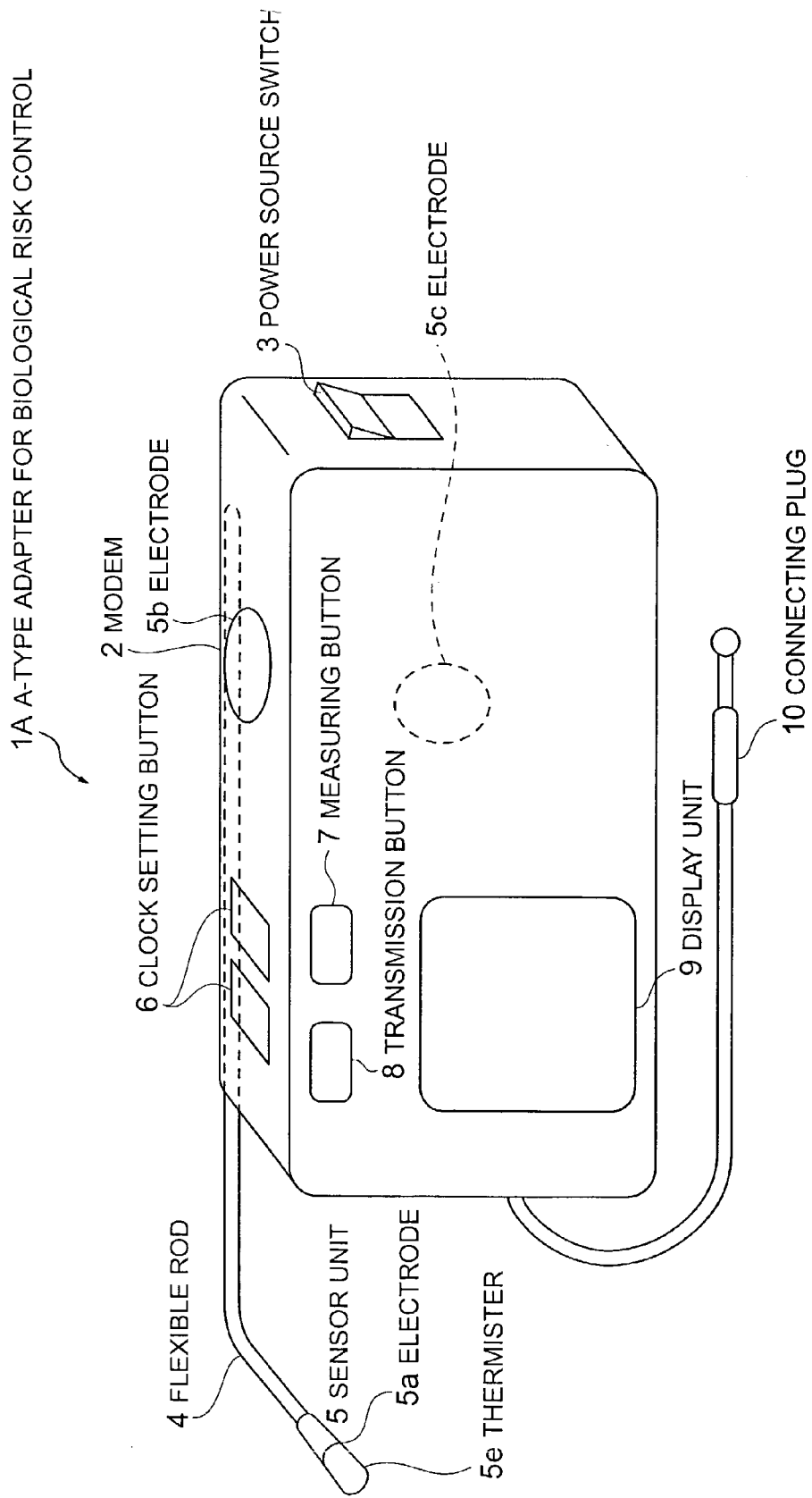
FIG. 6 is a diagram schematically showing a structure of an adapter for controlling biological risk described in JP 9-173304 A.

FIGS. 5A and 5B are respectively diagrams schematically showing the display contents of the display unit 17 in the compression display mode.

As shown in FIGS. 5A and 5B, in the portable biological data measuring apparatus of the present invention, the electrocardiographic waveform which is being displayed in the waveform display mode can be displayed with it being compressed in the direction of a time base.

Since the normal R wave has the frequency characteristics of about 20 Hz, when carrying out the compression display, the digital filtering processing (the normal band is in the range of 5 to 22 Hz) of removing the swinging of a base line to extract the R wave is executed.

When the electrocardiographic waveform is normal, the R—R intervals are equal to one another and the R waves are displayed in the portion above the base line. However, when some of the R waves are lacked due to an irregular pulse or the like, since as in a portion (3) within the compressed display, the R waves are displayed with the intervals of the R waves being spread as shown in FIG. 5A, the occurrence of an irregular pulse can be readily confirmed.

In addition, when an abnormal waveform is generated due to a ventricular extrasystole or the like, an abnormal waveform can be readily confirmed on the basis of the waveform being different from other waveforms, as in the displayed portion surrounded with a broken line in the compression display in FIG. 5A.

Next, the R—R graph display mode will hereinbelow be described.

The portable biological data measuring apparatus of the present invention has the R—R graph display mode for display of the transition of the number of heartbeats in the R—R intervals.

In the R—R graph display mode, as shown in a part (c) of FIG. 3, the transition of the number of heartbeats between R—R is displayed in the form of a graph in the coordinate system in which the axis of ordinate represents the number of heartbeats, and the axis of abscissa represents a time base.

As described above, in the R—R graph display mode of the portable biological data measuring apparatus of the present invention, since the transition of the number of heartbeats can be grasped visually, the disturbance in heart rate such as an irregular pulse can be readily confirmed.

Note that, as described above, in the portable biological data measuring apparatus of the present invention, the data of the measured electrocardiographic waveform can be stored and held in the electrocardiographic waveform storing unit 16. For example, in the case where the unit 16 is configured so as to be able to store and hold up to ten waveforms, when the eleventh waveform has been measured, the data of the oldest electrocardiographic waveform is erased to be able to store and hold the data of the newest electrocardiographic waveform in the electrocardiographic waveform storing unit 16. In such a manner, the data of the oldest electrocardiographic waveform can be successively replaced with the data of the newest electrocardiographic waveform, and also the data of the electrocardiographic waveform which is stored and held as described above can be displayed on the display unit 17 on the basis of the arbitrary selection among the above-mentioned three modes.

The portable biological data measuring apparatus according to the present invention comprises a GND electrode and a minus electrode which are provided on the opposite side faces of a roughly rectangular parallelopiped-shaped chassis, and a plus electrode provided on the face curved to have an ellipse shape and adjacent to the opposite faces on which the GND electrode and the minus electrode are provided, in which biological data is measured using the plus electrode, the GND electrode and the minus electrode. By adopting such a structure, it is possible to stably measure an electrocardiographic waveform.

In addition, the portable biological data measuring apparatus according to the present invention further comprises display means for displaying thereon the biological data, in which a first R wave and a second R wave contained in an electrocardiographic waveform are displayed on the display means, and in which an axis for reading-out of the number of heartbeats on which data representing the number of heartbeats is plotted is displayed on the axis of abscissa indicating a time base with the peak portion of the first R wave being set as a reference point. As a result, it is possible to provide a portable biological data measuring apparatus which is capable of reading out instantaneously the number of heartbeats.

In addition, the portable biological data measuring apparatus according to the present invention further comprises display means for displaying thereon the biological data, in which an electrocardiographic waveform is displayed on the display means with the waveform being compressed in the direction of a time base. As a result, it is possible to provide a portable biological data measuring apparatus with which the occurrence of an irregular pulse can be readily confirmed.

Moreover, the portable biological data measuring apparatus according to the present invention further comprises display means for displaying thereon the biological data, in which the data representing the time transition of the number of heartbeats between the adjacent R waves is displayed on the display means. As a result, it is possible to provide a portable biological data measuring apparatus with which the disturbance in heart rate such as an irregular pulse can be readily confirmed.

As many apparently widely different embodiments of this invention may be made without departing from the spirit and scope thereof, it is to be understood that the invention is not limited to the specific embodiment thereof except as defined in the appended claims.

What is claimed is:

1. A portable biological data measuring apparatus, comprising: a GND electrode (12B) and a minus electrode (12C) which are provided on the opposite side faces of a roughly rectangular parallelopiped-shaped chassis (11); a plus electrode (12A) provided on the face adjacent to the opposite faces on which said GND electrode (12B) and said minus electrode (12C) are provided, and display means (17) for displaying thereon the biological data, wherein an electrocardiographic waveform is displayed on said display means with the waveform being compressed in the direction of a time base, wherein said plus electrode (12A), said GND electrode (12B) and said minus electrode (12C) have irregularities in their surface and biological data is measured using said plus electrode (12A), said GND electrode (12B) and said minus electrode (12C) and said plus electrode is provided on an end face of said chassis that is curved to have an ellipse shape and is adjacent to the opposite faces on which the GND electrode and the minus electrode are disposed.

2. A portable biological data measuring apparatus according to claim 1, further comprising display means (17) for displaying thereon the biological data, wherein a first R wave and a second R wave contained in an electrocardiographic waveform are displayed on said display means, and wherein an axis (17a) for reading-out of the number of heartbeats on which data representing the number of heartbeats is plotted is displayed on the axis of abscissa indicating a time base with the peak portion of the first R wave being set as a reference point.

3. A portable biological data measuring apparatus according to claim 1, further comprising display means (17) for displaying thereon the biological data, wherein the data representing the time transition of the number of heartbeats between the adjacent R waves is displayed on said display means.

4. A portable biological data measuring apparatus, comprising: a GND electrode (12B) and a minus electrode (12C) which are provided on the opposite side faces of a roughly rectangular parallelopiped-shaped chassis (11); and a plus electrode (12A) provided on the face adjacent to the opposite faces on which said GND electrode (12B) and said minus electrode (12C) are provided, wherein said plus electrode (12A), said GND electrode (12B) and said minus electrode (12C) have irregularities in their surface and biological data is measured using said plus electrode (12A), said GND electrode (12B) and said minus electrode (12C) and said plus electrode is provided on an end face of said chassis that is curved to have an ellipse shape and is adjacent to the opposite faces on which the GND electrode and the minus electrode are diposed.

* * * * *